US009414789B2

(12) United States Patent
Soluri et al.

(10) Patent No.: US 9,414,789 B2
(45) Date of Patent: Aug. 16, 2016

(54) DIAGNOSTIC DEVICE FOR MORPHO-FUNCTIONAL INVESTIGATIONS

(71) Applicant: CONSIGLIO NAZIONALE DELLE RICERCHE (CNR), Rome (IT)

(72) Inventors: Alessandro Soluri, Rome (IT); Roberto Massari, Rome (IT)

(73) Assignee: CONSIGLIO NAZIONALE DELLE RICERCHE (C.N.R.), Rome (IT)

( * ) Notice: Subject to any disclaimer, the term of this patent is extended or adjusted under 35 U.S.C. 154(b) by 132 days.

(21) Appl. No.: 14/351,284

(22) PCT Filed: Oct. 11, 2012

(86) PCT No.: PCT/IT2012/000314
§ 371 (c)(1),
(2) Date: Apr. 11, 2014

(87) PCT Pub. No.: WO2013/054369
PCT Pub. Date: Apr. 18, 2013

(65) Prior Publication Data
US 2014/0378829 A1     Dec. 25, 2014

(30) Foreign Application Priority Data

Oct. 13, 2011   (IT) .............................. RM2011A0543

(51) Int. Cl.
*A61B 6/03*     (2006.01)
*A61B 6/04*     (2006.01)
*A61B 6/00*     (2006.01)
(52) U.S. Cl.
CPC . *A61B 6/03* (2013.01); *A61B 6/037* (2013.01); *A61B 6/0478* (2013.01); *A61B 6/4266* (2013.01); *A61B 6/4275* (2013.01); *A61B 6/4417* (2013.01); *A61B 6/035* (2013.01); *A61B 6/0421* (2013.01); *A61B 6/4411* (2013.01)

(58) Field of Classification Search
CPC .......... A61B 6/03; A61B 6/035; A61B 6/037; A61B 6/0421; A61B 6/0478
See application file for complete search history.

(56) References Cited

U.S. PATENT DOCUMENTS

| | | | | |
|---|---|---|---|---|
| 5,825,031 A * | 10/1998 | Wong | ...................... | G01T 1/164 250/363.03 |
| 2004/0129886 A1 * | 7/2004 | Lecoq | ..................... | G01T 1/202 250/363.03 |
| 2005/0263717 A1 | 12/2005 | Soluri et al. | | |
| 2007/0007455 A1 * | 1/2007 | Juni | ....................... | A61B 6/037 250/363.04 |
| 2008/0001089 A1 * | 1/2008 | Lusser | .................. | G01T 1/2018 250/363.02 |
| 2011/0084211 A1 * | 4/2011 | Yamaya | .................. | A61B 6/037 250/363.03 |
| 2011/0196223 A1 * | 8/2011 | Balakin | .................... | A61N 5/10 600/407 |
| 2012/0265050 A1 * | 10/2012 | Wang | ..................... | A61B 5/055 600/411 |

FOREIGN PATENT DOCUMENTS

DE   10 2009 054676 A1   6/2011
EP       2 138 866 A1   12/2009

OTHER PUBLICATIONS

International Search Report, dated Dec. 18, 2012, from corresponding PCT application.

* cited by examiner

*Primary Examiner* — Baisakhi Roy
(74) *Attorney, Agent, or Firm* — Young & Thompson

(57) ABSTRACT

A diagnostic device for morpho-functional investigations includes a plurality of measuring elements (5, 6, 7, 8, 9) of the scintillation type, positioned around a receiving area (3) for performing relative three-dimensional investigations on different parts of a patient (P) positioned in the receiving area, the first ring (5) having an internal diameter (d) less than the internal diameter (D) of the second ring (6).

20 Claims, 8 Drawing Sheets

DIAGNOSTIC DEVICE FOR MORPHO-FUNCTIONAL INVESTIGATIONS

TECHNICAL FIELD

This invention relates to a diagnostic device for morpho-functional investigations, specifically in the field of nuclear medicine, and in particular a tomography device of the PET (positron emission tomography) and/or SPECT (single-photon emission computed tomography) type, which can be integrated with a CT (Computerised Tomography) device.

BACKGROUND ART

Different types of diagnostic devices are known in nuclear medicine. Amongst these there are the scintillation devices which basically include two categories of devices: the PET diagnostic devices and the SPECT diagnostic devices The PET type diagnostic devices comprise a couch on which the patient lies and a measuring system with an annular shape which surrounds the patient. The couch can move axially through the measuring system for making a three-dimensional measurement. The annular measuring system has a succession of scintillation measurement devices positioned along the annular extension for identifying the antiparallel scintillation events typical of the PET technology.

The geometry used allows the patient to have a comfortable supporting surface during the examination, the duration of which can, normally, vary on the basis of the scanning area and which on average can vary from 20 to 30 minutes.

The types of devices for SPECT diagnostics also comprise a couch on which the patient lies but the measuring system does not use a ring-type geometry but adopts a square shape and rotates about a horizontal axis to perform a complete circular scan around the patient.

In the SPECT technology, the number of measuring systems normally varies as a function of the speed with which the examination is to be performed, so two or three measurement modules are often used simultaneously (normally positioned on a same rotatable support and spaced at angular intervals about the axis of rotation) for allowing a reduction in the acquisition times. The acquisition time, which varies as a function of the area to be analysed, results in lengthy times during which the patient must remain still. The standard geometry used therefore aims to acquire images in such a way that the patient remains still in the initial position and therefore avoids that a movement of the patient can change the acquisition geometry, introducing alterations to the final images produced. In this way, the use of a couch on which the patient can lie to remain still for long periods of time can ensure the achievement of this aim.

The technologies currently used therefore contemplate a use, in terms of occupation of spaces, which is certainly large, having to ensure the movement of a couch through the scanning ring and the relative shielding. Typically, the device is positioned at the centre of a medium-sized room and its installation requires a considerable overall size, to which it is necessary to add all the dimensions of the shielding systems.

To these techniques of a functional nature, the morphological technique is often also added relative to a computerised tomography TC.

Moreover, according to the current state of the art, the technologies used for performing the above-mentioned morpho-functional investigations are all oriented towards the making of devices which are able to obtain very high quality spatial resolutions. This, however, clashes with the fact that the annular measuring systems used are often designed for scanning the entire body, considering the average abdomen and chest dimensions of the patient. Generally, the dimensions of the internal diameter can be approximately 80 cm. With this reference dimension, even much smaller organs can be detected, but providing values with a lower spatial resolution, which cannot exploit the optimisations of the acquisition geometry for the specific investigation.

Moreover, the speed with which the diagnostic investigation is performed represents an important aspect in economic terms and for the management of the scintigraphic examinations.

These techniques have time limitations linked to the rapid decay of the activities of the radiopharmaceuticals (radioisotopes) used. Besides, the rapid developments resulting from research into radiopharmaceuticals have lead to increasingly specific radiopharmaceuticals linked to specific diseases. It is to be desired, however, that the use of these radiopharmaceuticals is not penalised by the excessive duration of the diagnostic examinations which could compromise the correct outcome of the examination due to the excessive decay of the pharmaceutical.

DISCLOSURE OF THE INVENTION

In this context, the technical purpose which forms the basis of this invention is to provide a diagnostic device for morpho-functional investigations that overcomes the above-mentioned disadvantages of the prior art.

In particular, the aim of this invention is to provide a diagnostic device for morpho-functional investigations which is able to perform investigations on different parts of the body of a patient whilst maintaining a high spatial resolution.

The aim of this invention is also to provide a diagnostic device for morpho-functional investigations which has reduced dimensions thereby needing reduced installation operations (for example, for the shielding).

The aim of this invention is also to provide a diagnostic device for morpho-functional investigations which has fast investigation speeds.

The technical purpose indicated and the aims specified are substantially achieved by a diagnostic device for morpho-functional investigations comprising the technical features described in one or more of the appended claims.

BRIEF DESCRIPTION OF THE DRAWINGS

Further features and advantages of the invention are more apparent in the non-limiting description which follows of a preferred embodiment of a diagnostic device for morpho-functional investigations as illustrated in the accompanying drawings, in which.

DETAILED DESCRIPTION OF THE PREFERRED EMBODIMENTS OF THE INVENTION

Figure 1:
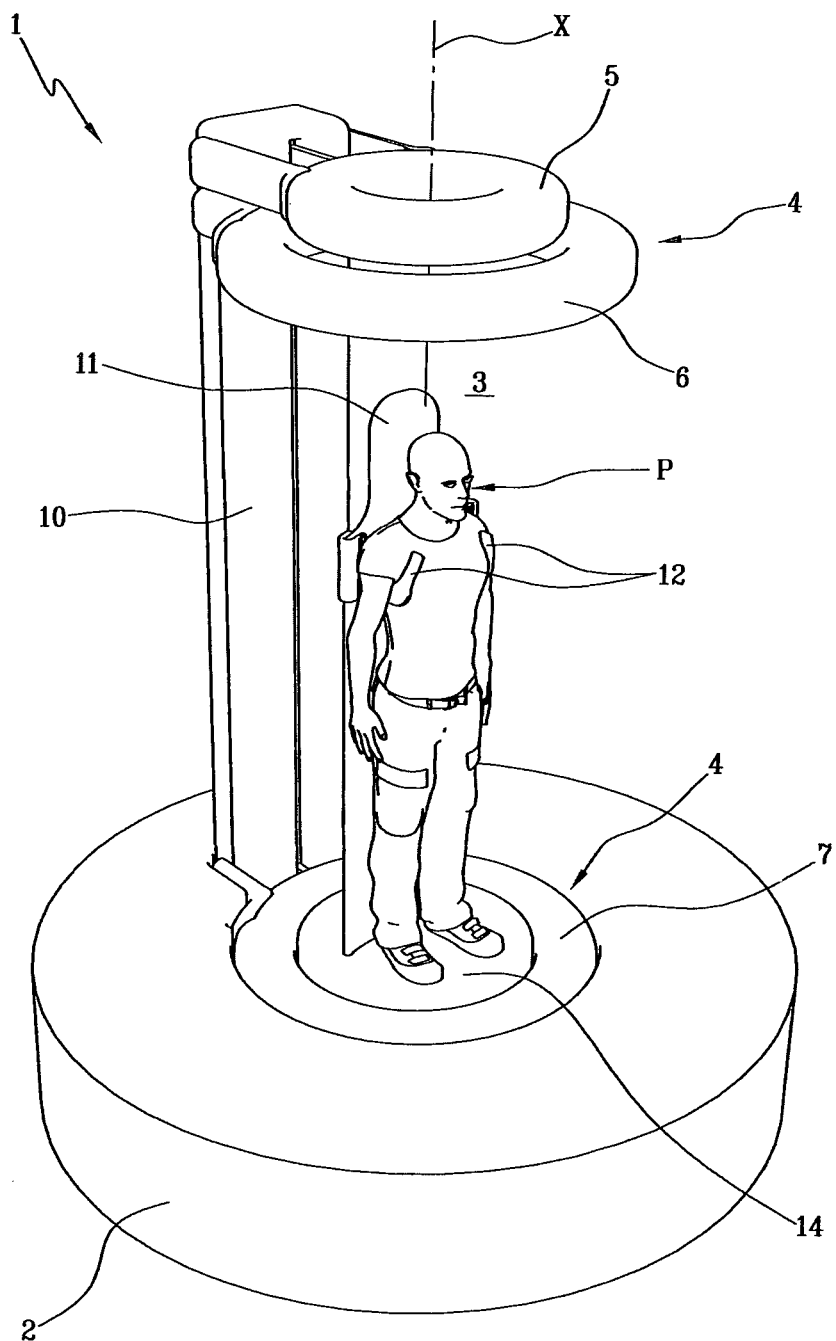
FIG. 1 is a perspective view of a diagnostic device according to this invention in a first embodiment of it.
Figure 2:
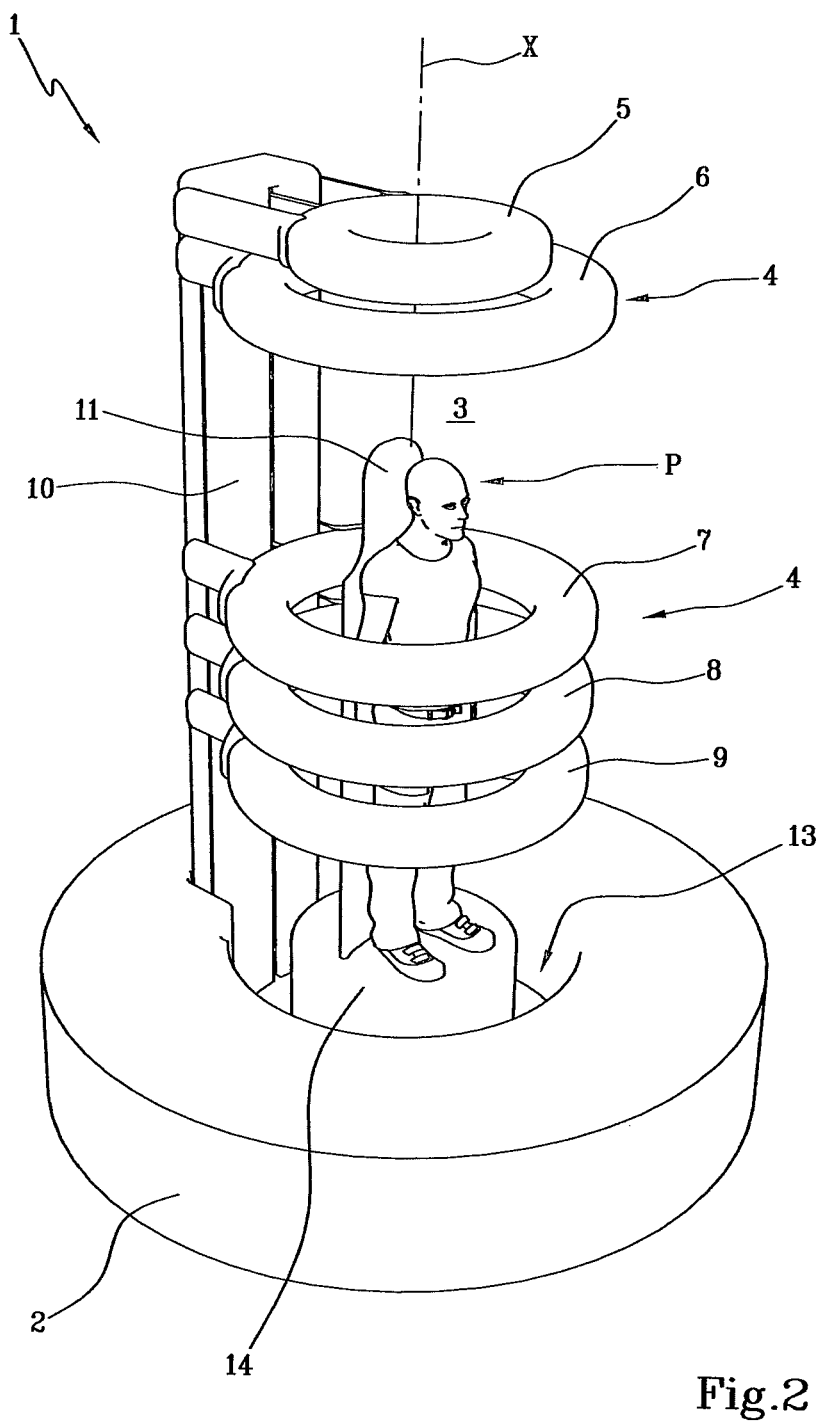
FIG. 2 is a perspective view of the device of FIG. 1 in a different operating condition.

With reference to the accompanying drawings, the numeral 1 denotes in its entirety a diagnostic device according to this invention.

In all the different embodiments described, the device 1 comprises a base 2, that can be rested on supporting surface and having a receiving area (3) designed to receive a patient "P" during a diagnostic investigation treatment.

Measuring means 4 for performing a diagnostic investigation of at least a part of a patient "P" positioned in the receiving area 3 are mounted on the base 2.

In particular, as shown in all the embodiments illustrated, the measuring means 4 comprise at least a first and a second measuring ring 5, 6 positioned around the receiving area, that is to say, extending circumferentially around the receiving area.

Preferably, each measuring ring 5, 6 is axisymmetric in shape about a respective axis "X". That is to say, the measuring rings 5, 6 extend on a circular line, adopting a toroidal shape. This allows the rings 5, 6 to scan 360° of a specific part of the patient "P".

Preferably, in that configuration the axis "X" of the rings 5, 6 coincides with a direction of extension of the receiving area 3.

In the accompanying drawings, the measuring rings 5, 6 are mounted on the base 2 in such a way that the respective axes "X" are parallel to each other and, in particular, coincident.

The toroidal shape of the measuring rings 5, 6 defines, for each ring 5, 6, a central opening having a dimension (diameter) corresponding to the internal diameter "d, D" of the ring 5, 6.

Advantageously, the first measuring ring 5 has an internal diameter "d" less than the internal diameter "D" of the second measuring ring 6. Preferably, the internal diameter "d" of the first measuring ring 5 is approximately equal to half the internal diameter "D" of the second measuring ring 6.

Advantageously, the internal diameter "d" of the first measuring ring 5 is such as to be slightly greater than the maximum transversal dimension of the head of a user, and preferably between 30 and 50 cm and still more preferably equal to approximately 40 cm.

The internal diameter "D" of the second measuring ring 6, on the other hand, is such as to be slightly greater than the maximum transversal dimension of the bust of a user, and preferably between 60 and 100 cm and still more preferably equal to approximately 80 cm.

Consequently, the first measuring ring 5 has a geometry optimised to achieve an optimum spatial resolution in investigations on small organs (head or limbs), for staying very close to it, whilst the second measuring ring 6 has a geometry optimised to achieve an optimum spatial resolution on parts of the patient having larger dimensions (for example, the bust).

Preferably, the measuring means 4 also comprise one or more further measuring rings for increasing the measuring area or for reducing the investigation time.

As shown in the accompanying drawings, there is a third measuring ring 7 the geometry of which is preferably identical or substantially identical to that of the second measuring ring 6 and it is therefore also optimised to perform investigations on the bust of the patient "P".

The third measuring ring 7 also has the respective axis parallel to and preferably coincident with the axes of the other two rings 5, 6 and it is also, therefore, positioned around the receiving area 3.

Moreover, in some embodiments illustrated, there can be other rings, in particular a fourth and a fifth measuring ring 8, 9 as described below.

The base 2 comprises a support structure 10 extending along the receiving area 3, therefore along the above-mentioned axes "X" of the measuring rings 5, 6, 7, 8, 9.

The first ring 5 is located on the support structure 10 in a position corresponding, or designed to correspond, to a portion of the receiving area 3 designed to receive the head of a patient "P" whilst the second ring is located in a position corresponding, or designed to correspond, to a portion of the receiving area 3 designed to receive the bust of the patient "P".

Advantageously, the measuring rings 5, 6, 7, 8, 9 are slidably mounted on the support structure 10 to move along it, in particular along the axis "X".

Thanks to that sliding connection, the measuring rings 5, 6, 7, 8, 9 can be moved along the body of the patient "P" to perform the desired three-dimensional scanning and they can therefore be moved between an inactive position, wherein they are positioned at the ends of the receiving area 3 (allowing the patient to access or leave the receiving area 3), and an operating position wherein one or more of them engages the receiving area 3 for performing the scan.

Preferably, the measuring rings 5, 6, 7, 8, 9 are moved independently from each other (by motor means not illustrated) along the support structure 10.

Notwithstanding the possibility to move measuring rings 5, 6, 7, 8, 9, the first measuring ring 5 still remains located in a position such as to perform the scanning of the head of the patient "P" positioned in the receiving area 3. To do that, it is preferable that the first measuring ring 5 in the above-mentioned inactive position positions itself at the end of the receiving area 3 facing towards the head of the patient "P".

Some of the measuring rings 5, 6, 7, 8, 9 are of the scintillation type, that is, of the type designed in such a way as to receive a radiation (emitted by a radiopharmaceutical taken by the patient according to known methods) and transform that radiation into a luminous radiation (photons) which can be measured by special optoelectronic instrumentation (for example, phototubes, silicon photomultipliers, semiconductors or photodiodes) for calculating the position and the energy of the interacting photons and transferring that information to a conversion device and then to an electronic processor which process and displays it on a monitor in the form of an image.

In particular, as will become evident by the different embodiments described below, the measuring rings of the scintillation type are those designed to perform PET or SPECT type investigations. There can, however, be a measuring ring for CT investigations which, by their very nature, do not use the physics principle of scintillation.

FIGS. 1 to 4 show a first embodiment of the diagnostic device according to this invention.

According to this embodiment, the receiving area 3 extends vertically. In that configuration, the support structure 10 extends vertically whilst the measuring rings 5, 6, 7, 8, 9 are positioned according to respective horizontal or substantially horizontal planes.

That shape of the device 1 allows diagnostic investigations to be performed on a patient "P" standing up. To facilitate the patient "P" keeping a correct erect posture, the base preferably comprises a backrest 11, substantially vertical and preferably with an anatomical shape, designed to form a support surface for the back of the patient "P".

In order to further facilitate the adoption of the correct erect posture by the patient "P", the backrest 11 can be equipped with stabilisation protrusions 12, preferably curved, designed for insertion beneath the armpits of the patient "P" blocking him/her in the correct posture (FIG. 1). The protrusions 12 are designed to form a contact point and a stable gripping point for the patient "P" and designed to keep the patient "P" in a predetermined correct posture suitable for the diagnostic investigation.

Moreover, according to this configuration the base 2 may comprise an annular cavity 13 (FIG. 2) into which one or more measuring rings 7, 8, 9 are inserted, in a concealed manner. Inside the annular seat 13 there is a raised element 14 on which the patient "P" rests directly in the erect posture (FIG. 1).

The first measuring ring 5, and, preferably, also the second measuring ring 6, have, on the other hand, their relative inactive position in the top part of the receiving area 3, so, above the patient "P".

Figure 3:
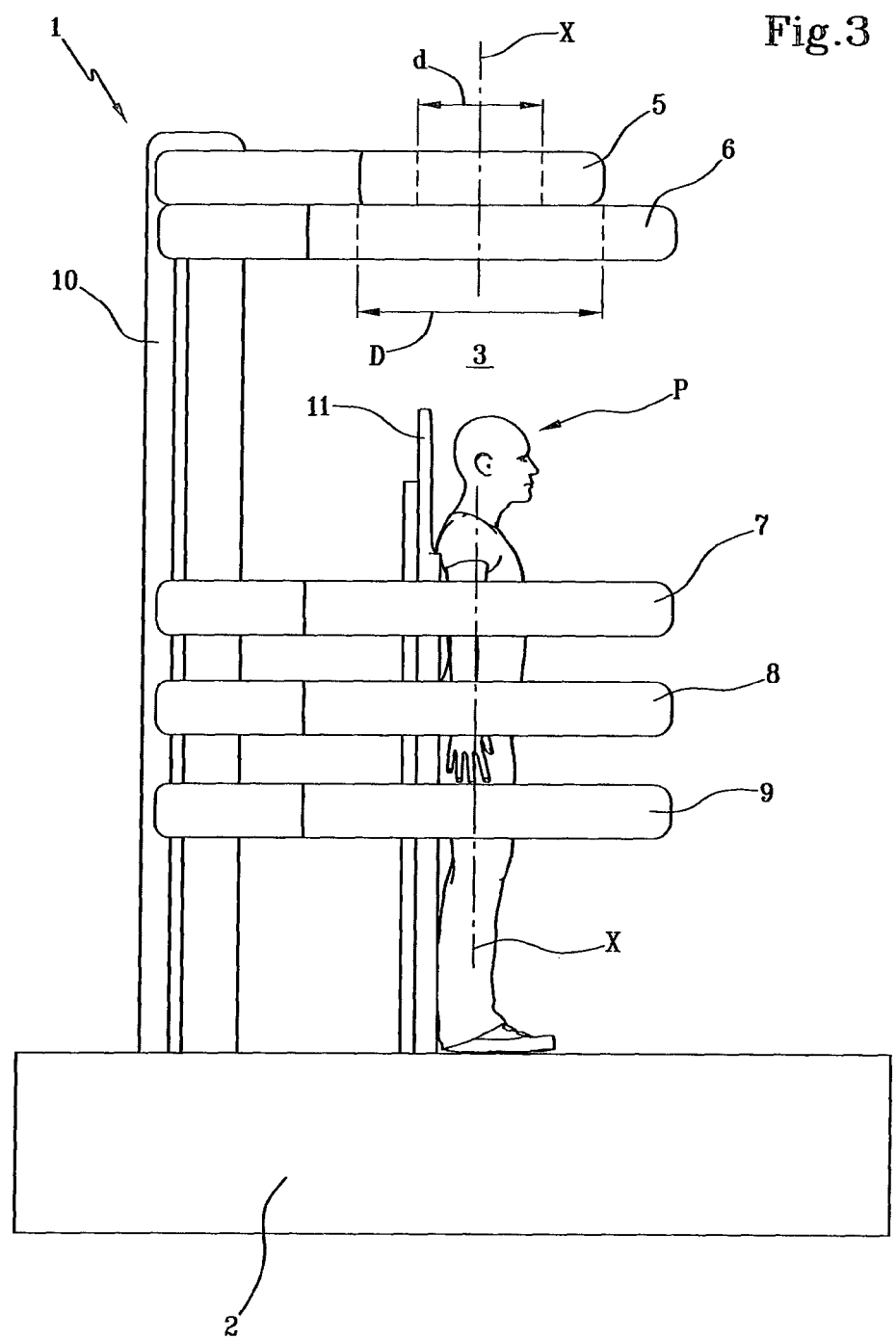
FIG. 3 is a side view of the device of FIG. 2 in the same operating condition.

FIG. 3 shows the device 1 in a vertical configuration with the first and the second measuring rings 5, 6 inactive whilst the other measuring rings 7, 8, 9 are raised and positioned around the bust of the patient "P" for performing, simultaneously, the desired diagnostic investigation.

Preferably, the dimension of the measuring rings 5, 6, 7, 8, 9 (at least the dimension of the rings 6, 7, 8, 9) in an axial direction, that is, along the relative direction of movement, is between 10 and 20 cm and still more preferably equal to approximately 15 cm. Therefore, by providing a distance between the above-mentioned third, fourth and fifth rings 7, 8, 9 of approximately 10-15 cm, an almost complete coverage of the bust of the patient "P" can be obtained and the entire measurement performed in very little time.

Figure 4:
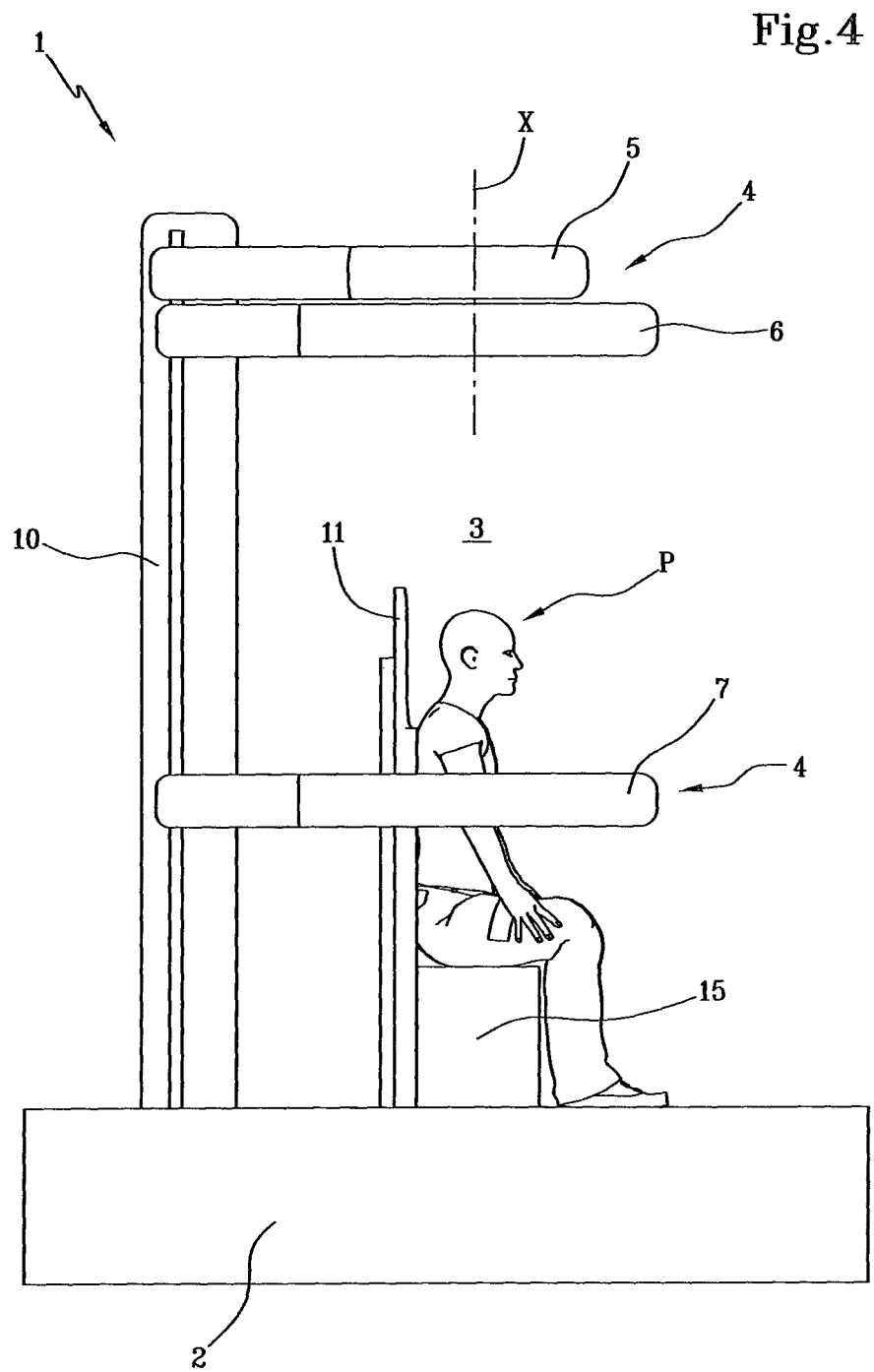
FIGS. 4 and 5 are side views of a diagnostic device according to this invention in a second embodiment of it and in two different operating conditions.
Figure 5:
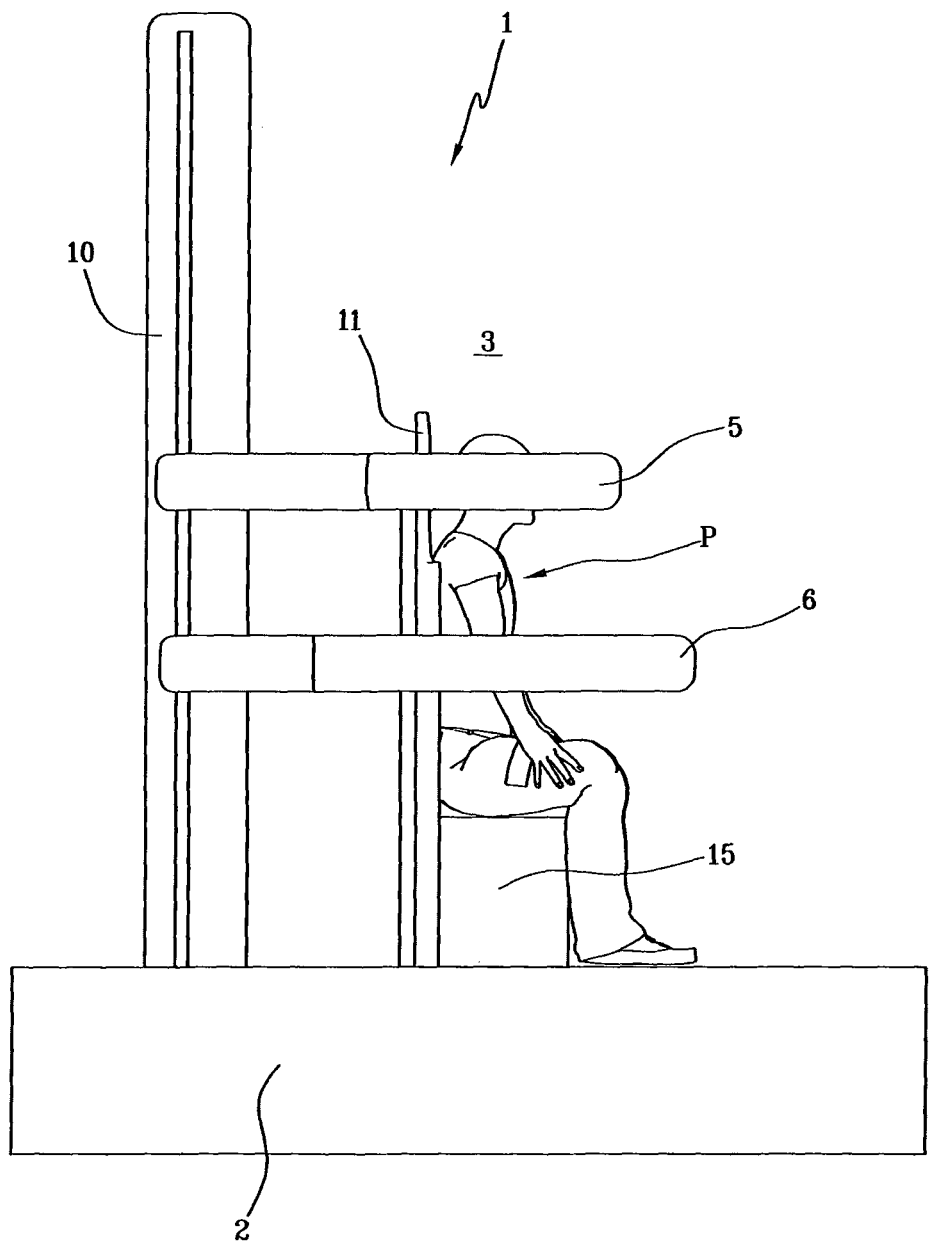

FIGS. 4 and 5 show a second embodiment of the diagnostic device according to this invention.

In this second embodiment, the receiving area 3 is again positioned substantially vertically but in this case the base 2 has a seat 15 (an anatomic seat, an exercise bike for stress tests, a stool or the like) for positioning the patient "P" in a seated position. Apart from this difference, and, if necessary, a height less than that of the embodiment described above, the device is structurally identical to that of FIGS. 1 to 3.

In more detail, FIG. 4 shows the device 1 with the third measuring ring 7 raised for performing a diagnostic investigation on the bust of the patient "P" whilst FIG. 5 shows the activation of the first and the second measuring rings 5, 6 for performing diagnostic investigations, respectively, on the head and the bust of the patient "P".

Figure 6:
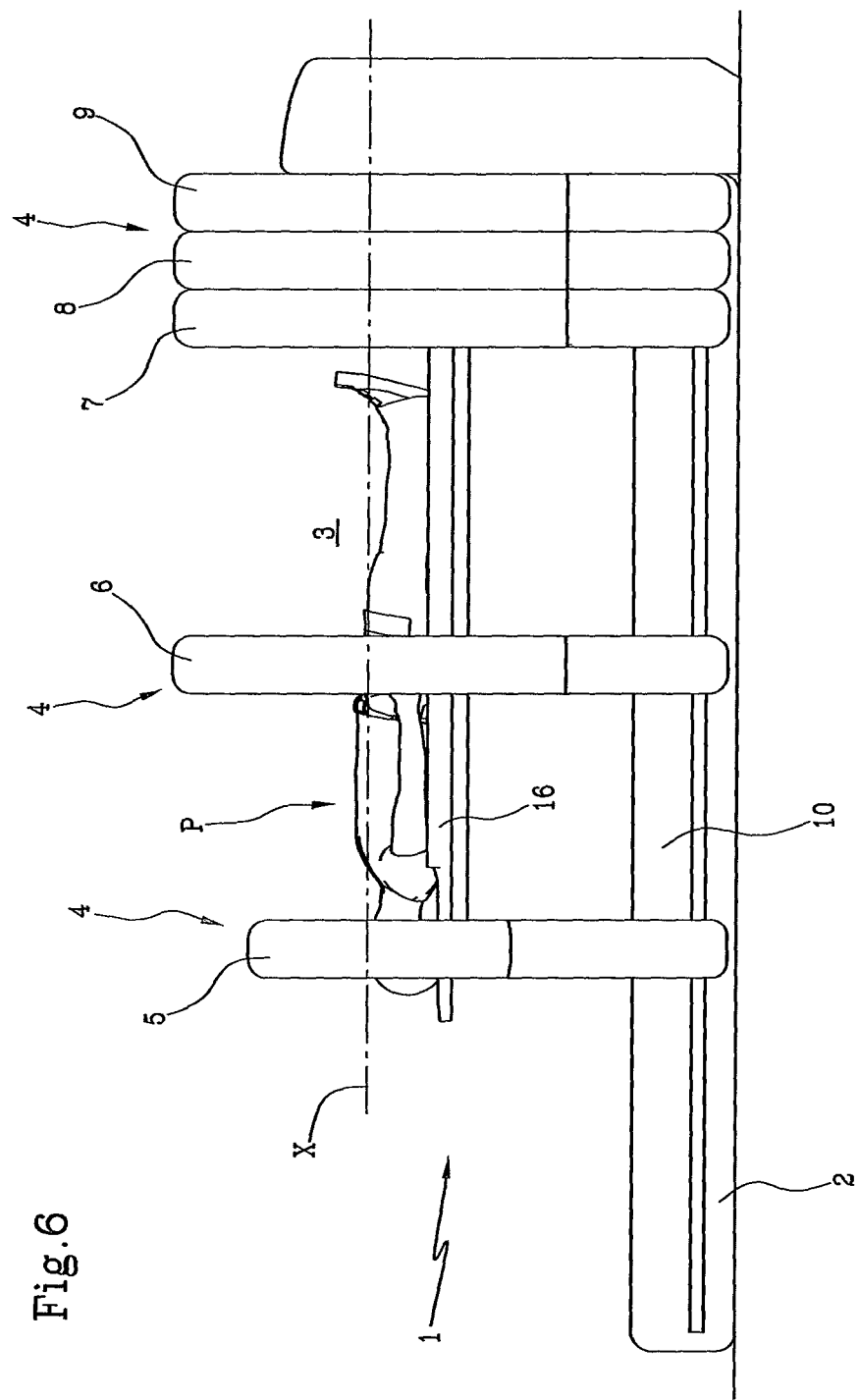
FIGS. 6 and 7 are side views of a diagnostic device according to this invention in a third embodiment of it and in two different operating conditions.
Figure 7:
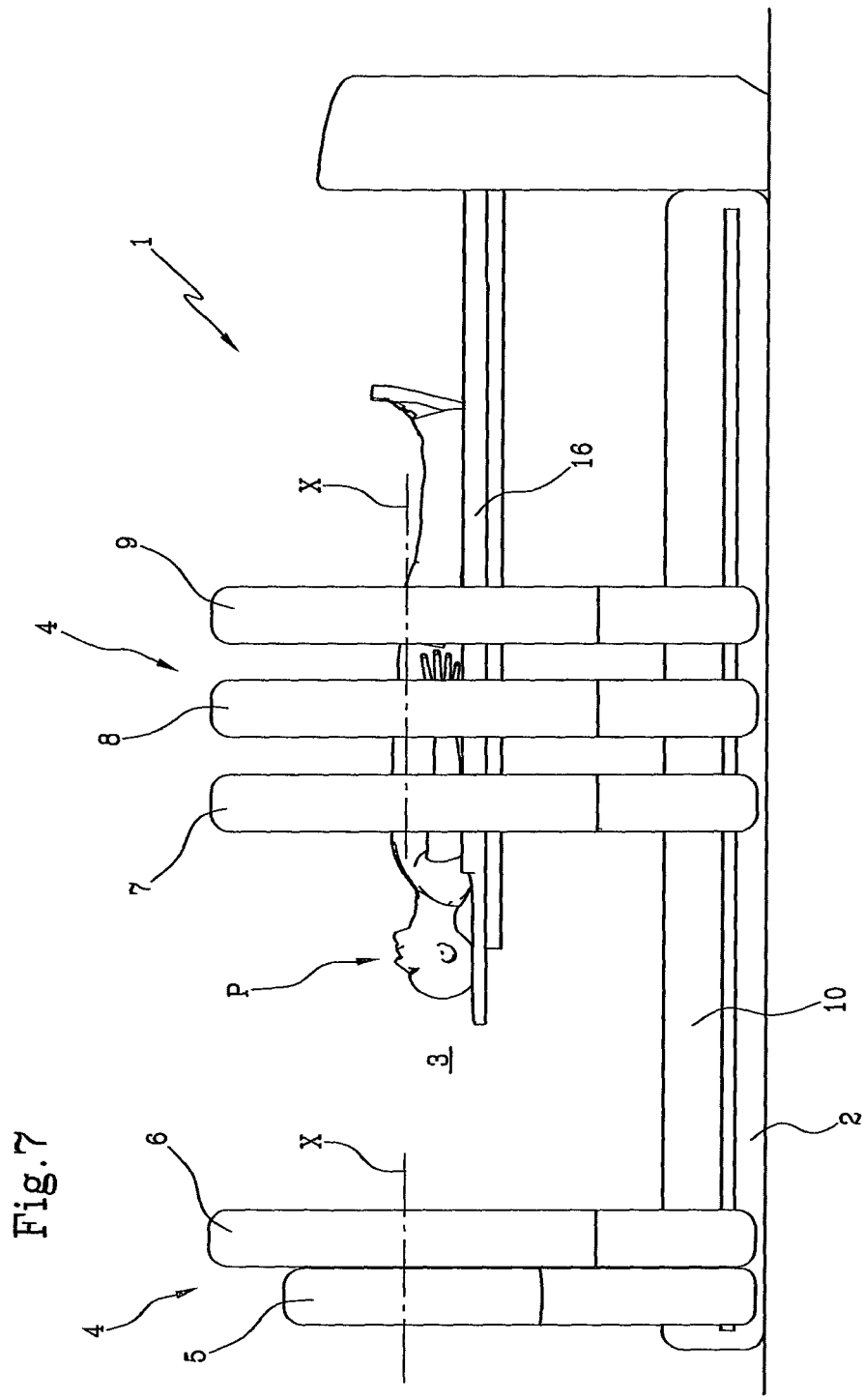

FIGS. 6 and 7 show a third embodiment of the diagnostic device according to this invention.

This embodiment differs from the previous embodiments in that it has a couch 16 designed to position the patient "P" in a lying down posture. Therefore, the receiving area 3 extends horizontally and the measuring rings 5, 6, 7, 8, 9 are positioned according to respective vertical or substantially vertical planes.

That means that the support structure 10 extends horizontally, preferably at the base of the device 1, and allows a horizontal translation of the measurement rings 5, 6, 7, 8, 9. In more detail, FIG. 6 shows the activation of the first and the second measuring rings 5, 6 for performing diagnostic investigations, respectively, on the head and bust of the patient "P" whilst FIG. 7 shows the activation of the third, fourth and fifth measuring rings 7, 8, 9 for performing a diagnostic investigation on the bust of the patient "P".

Advantageously, the third measuring ring 7 can be designed to perform an investigation of a different type and/or on a different part of the patient "P" with respect to the first and/or second measuring rings 5, 6.

In particular, according to a preferred embodiment of the invention and according to methods applicable to all the embodiments described and illustrated above, the first measuring ring 5 performs a functional diagnostic investigation of the PET type for dedicated organs whilst the second measuring ring 6 performs a morphological TC investigation. The other measuring rings 7, 8, 9 can perform a PET type investigation, allowing the speed of the PET type investigations to be increased or to increase the investigation area, or they can be configured in such a way as to perform a SPECT type investigation.

Alternatively, the first measuring ring 5 can be configured for SPECT type diagnostic investigations.

In a different embodiment, keeping the first measuring ring 5 configured for functional diagnostic investigations of the PET type, the second measuring ring 6 can be configured for diagnostic investigations of the PET or SPECT type.

According to further embodiments not illustrated, the receiving area 3 extends along a direction inclined with respect to the horizontal and the measuring rings 5, 6, 7, 8, 9 are positioned according to respective inclined planes, in particular according to any plane between a horizontal plane and a vertical plane.

Advantageously, the measuring rings 5, 6, 7, 8, 9 are removably applied to the support structure 10 and are interchangeable with corresponding substitute rings to allow a change of the type of investigation to be performed.

For example, the second measuring ring 6 originally configured for CT type investigations can be replaced with a second measuring ring configured for SPECT or PET type investigations.

For these reasons, the device according to this invention is equipped with:
- a pair of first rings 5 with a reduced diameter (approximately 40 cm), one of the PET type and the other of the SPECT type;
- a ring with a larger diameter (approximately 80 cm) for morphological TC investigations (preferably for use as second ring 6); and
- a plurality of rings also with a larger diameter (approximately 80 cm), some of which of the PET type and others of the SPECT type, selectively mountable on the support structure 10 according to specific needs.

Figure 8:
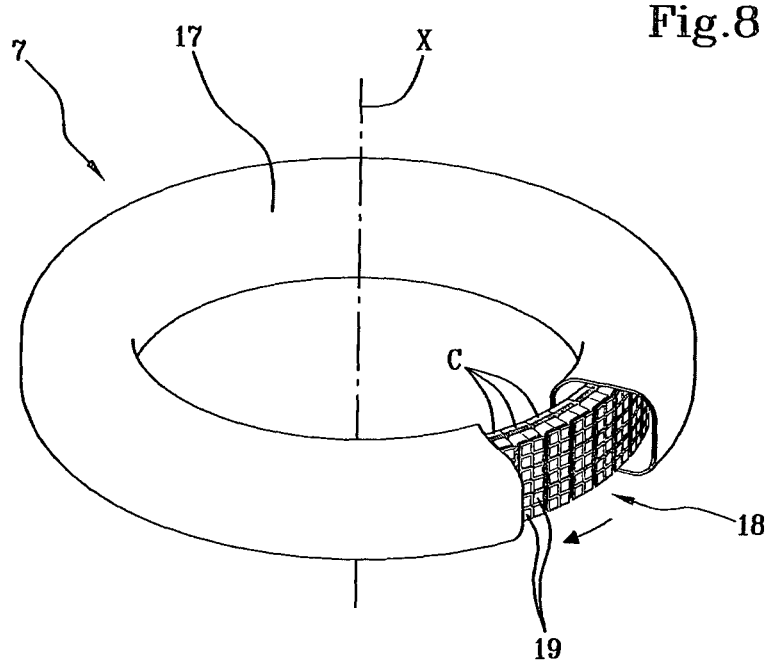
FIGS. 8 and 9 are perspectives, partly a view and partly a cross-section, of a detail of the diagnostic device according to this invention and in two different operating conditions.
Figure 9:
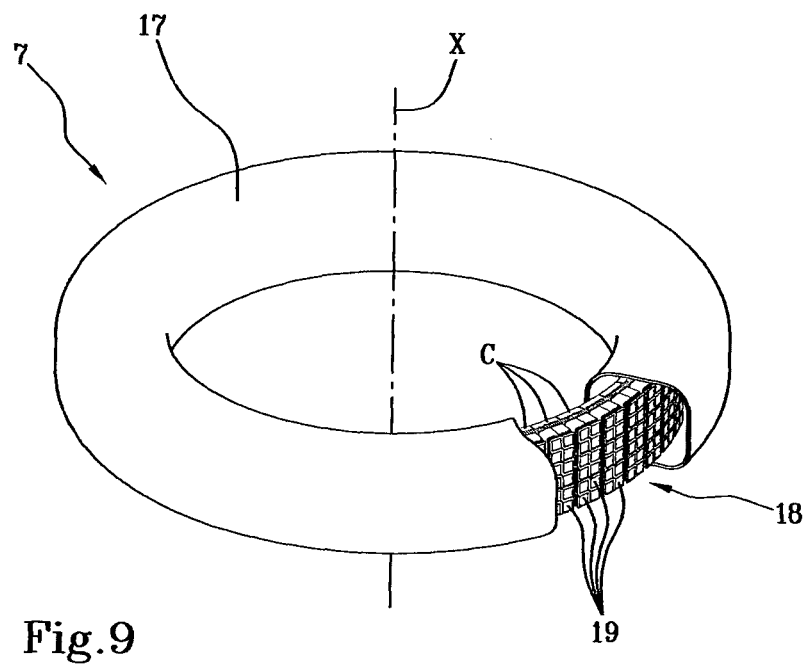

The performance of an investigation of the SPECT type using a measuring ring of the type described above can be obtained by giving the ring a structure of the type illustrated in FIGS. 8 and 9. The embodiment illustrated refers to the third measuring ring 7, however the teachings shown can be implemented for any of the measuring rings 5, 6, 7, 8, 9 presented.

In more detail, the ring 7 for SPECT investigations comprises an outer casing 17 with an annular shape and a measuring body 18, included inside the outer casing 17 and movable relative to it for rotating around the axis "X" of the measuring ring 7 and therefore around the receiving area 3 (and therefore around the patient "P"), in such a way as to acquire at least two images rotated between each other by a predetermined angle.

In more detail, the measuring body 18 comprises a succession of scintillation elements (19), each equipped with a respective scintillation crystal and positioned according to an annular distribution facing towards the axis "X" in such a way that the scintillation crystals can receive the radiation emitted from an area corresponding to the axis "X".

The scintillation body also comprises a collimator "C" designed to absorb the radiation, emitted by the radiopharmaceutical taken by the patient, directed according to undesired angles and, in particular, outside a predetermined angle determined as a function of the spatial resolution to be given to the measuring body 18.

The presence of the collimator "C" is necessary due to the different emission process of the SPECT technology which, comprising the emission of single photons (unlike the antiparallel emission of the PET technology), requires the collimation in order to filter the radiation excessively inclined relative to the axis of the scintillation crystals.

The structure of the collimator "C" therefore follows the known principles of collimation and is not described in further detail.

The measuring body 18 rotates for an angular extension less than the dimension of the scintillation crystals, in such a way as to achieve the so-called "super resolution".

In other words, the ring 7 is rotated by a small amount corresponding to a movement of the scintillation crystals equal to half their dimension (or by the value of the intrinsic spatial resolution of the device).

For example, using square scintillation crystals with 5 mm sides, the rotation about the "X" axis will be such as to move the scintillation crystals laterally by 2.5 mm.

The rotation of the measuring body 18 can be obtained by rotating the latter relative to the outer casing 17 or by rotating the entire measuring ring 7.

Preferably, the above-mentioned rotation of the ring (or in any case of the scintillating elements for obtaining their lateral movement), aimed at achieving the super resolution, can also be performed on the rings designed for the PET technique.

Therefore, the structure illustrated in FIGS. 8 and 9 can also be used on the rings designed for PET investigations (except for the absence, in this case, of the collimator).

The use of a CT type measuring structure positioned on one of the measuring rings 5, 6, 7, 8, 9 allows data to be obtained on the morphology which can be used to correct the attenuation of tissues in PET investigations and favour the technique for merging morpho-functional images.

In particular, the solution which comprises the first measuring ring 5 configured for PET investigations and the second measuring ring 6 configured for CT investigations would be particularly advantageous.

According to variant embodiments with further advantages, some solutions specifically aimed at optimising the resolution (and suitably adapted to the circular geometry of the measuring rings) can be integrated inside one or more measuring rings, such as, for example:

variable collimation systems, which can be integrated in a SPECT ring, for example, a system of the type described in patent application no. RM2004A000271 of 31 May 2004 (U.S. Pat. No. 7,274,022 of 25 Sep. 2007) by the same Applicant. According to this configuration, the collimator "C" comprises a plurality of independent collimation elements, each associated with a corresponding scintillation element 19 and movable independently from the other collimation elements for varying the collimation length associated with the relative scintillation element 19.

super-resolution systems, which can be integrated in a PET or SPECT ring, for example, a system of the type described in patent application no. MI 2008A001798 of 10 Oct. 2008 (U.S. Pat. No. 7,939,807 B2 of 10 May 2011) and in patent application RM2009A000666 of 18 Dec. 2009 (US patent 2011/0163235 A1) by the same Applicant.

The invention achieves the aims set by overcoming the above-mentioned disadvantages of the prior art.

With the device according to this invention the patient is positioned in an erect or seated position relative to the measuring rings. At the same time, this geometry occupies less space and resolves certain clinical problems linked with the acquisition geometry with PET and SPECT techniques on dedicated organs. The versatility of the device allows several scintigraphic rings of the same or different technology to be used, integrating it with standard CT modules. This use is also possible on horizontal configurations of the device, that is to say, provided with a couch for supporting the patient in a lying down position.

The simultaneous use of several measuring rings also considerably reduces the investigation times, allowing the use of radiopharmaceuticals having a low decay time and/or a smaller dose of radiopharmaceutical to be taken by the patient.

Another element which characterises the device consists in the possibility to integrate, in one or more measuring rings, variable collimation solutions and super resolution adapted to the circular geometry in the SPECT technology and the super resolution technique in the PET technology.

The invention claimed is:

1. A diagnostic device for morpho-functional investigations, comprising:

a base having a receiving area designed to receive a patient during a diagnostic investigation treatment; and measuring means mounted on the base for performing a diagnostic investigation of at least a part of the patient (P) positioned in the receiving area, wherein the measuring means comprise at least a first measuring ring, a second measuring ring and a third measuring ring, said measuring rings being positioned around the receiving area and designed to perform relative investigations on different parts of the patient, the first measuring ring being of the scintillation type and having an internal diameter less than the internal diameter of the second measuring ring and of the third measuring ring, wherein the base comprises a support structure on which the measuring rings are applied, the first measuring ring being located in a position corresponding to a portion of the receiving area designed to receive the head of the patient and the second and third measuring rings being located in a position corresponding to a portion of the receiving area designed to receive the bust of the patient, and wherein the measuring rings are positioned according to respective substantially horizontal planes, wherein the support structure extends in a substantially vertical direction for positioning the first measuring ring above the second and third measuring rings, and wherein one of the second and third measuring rings is designed to perform only a PET type investigation and comprises an annular outer case and a succession of scintillation elements located within the annular outer case, whilst the other of the second and third measuring rings is designed to perform only a SPECT type investigation, said second and third measuring rings being configured to be selectively activated or deactivated depending upon a specific detection to be carried out on the patient, with the deactivated ring remaining lowered or raised above the head level of the patient.

2. The device according to claim 1, further comprising at least one backrest to form a stable support for the back of the patient positioned inside the receiving area both when standing up and when sitting down.

3. The device according to claim 2, wherein the backrest comprises a pair of stabilization protrusions designed to form a contact point and a stable gripping point for the patient and designed to keep the patient in a predetermined posture suitable for the diagnostic investigation.

4. The device according to claim 1, wherein the measuring rings are slidably mounted on the support structure to slide along the support structure in such a way as to perform a three-dimensional investigation along the body of the patient positioned in the receiving area.

5. The device according to claim 4, further comprising motor means associated with the measuring rings for moving each of the measuring rings independently along the support structure.

6. The device according to claim 1, wherein the internal diameter of the first measuring ring is greater than the maximum transversal dimension of the head of the patient.

7. The device according to claim 6, wherein the internal diameter of the second and third measuring rings is greater than the maximum transversal dimension of the bust of the patient.

8. The device according to claim 1, wherein the measuring rings extend around relative axes, preferably in an axially symmetric fashion, and wherein the axes are parallel to each other and preferably coincident.

9. The device according to claim 1, wherein,
the second measuring ring is designed to perform the PET type investigation and comprises the annular outer case and the succession of scintillation elements located within the annular outer case, the succession of scintillation elements being movable laterally by rotating around the receiving area in such a way as to acquire at least two images rotated between each other by a predetermined angle, and
the third measuring ring is designed to perform a SPECT type investigation and comprises another annular outer case and another succession of scintillation elements associated with a collimator and included inside the another annular outer case, the another succession of scintillation elements being movable laterally by rotating around the receiving area in such a way as to acquire at least two further images rotated between each other by a predetermined angle.

10. The device according to claim 9, wherein the collimator comprises a plurality of variable length collimation elements, independent from each other and each associated with a corresponding scintillation element, the collimation elements being movable independently to each other for identifying a specific variable collimation length for each scintillation element.

11. The device according to claim 1, further comprising a fourth measuring ring, designed to perform only a CT investigation and located in a position corresponding to a portion of the receiving area designed to receive the bust of the patient.

12. The device according to claim 1, wherein the internal diameter of the first measuring ring is between 30 and 50 cm.

13. The device according to claim 12, wherein the internal diameter of each of the second and third measuring rings is between 60 and 100 cm.

14. The device according to claim 12, wherein the internal diameter of each of the second and third measuring rings is equal to 80 cm.

15. The device according to claim 1, wherein the internal diameter of the first measuring ring is equal to 40 cm.

16. The device according to claim 1, wherein,
each of the measuring rings is axisymmetric in shape about a common axis that coincides with a direction of extension of the receiving area, such that the each of the measuring rings extend on a circular line, adopting a toroidal shape,
an internal diameter of the first measuring ring being between 30 and 50 cm,
an internal diameter of each of the second and third measuring rings being between 60 and 100 cm,
wherein the support structure supports the first measuring ring (5) above the second and third measuring, the measuring rings being independently movable along the common axis, and
the second measuring ring is structured to performs the PET type investigation for dedicated organs while the third measuring ring performs only one morphological investigation other than the PET type investigation.

17. A diagnostic device for morpho-functional investigations, comprising:
a base having a patient receiving area and a support structure; and
measuring means mounted on the base for performing a diagnostic investigation of the patient (P) positioned in the receiving area,
wherein the measuring means comprise at least a first measuring ring, a second measuring ring, and a third measuring ring movably mounted on the support structure and positionable according to respective substantially horizontal planes around the receiving area to perform relative investigations on different parts of the patient, with the first measuring ring being positionable in a position corresponding to a portion of the receiving area designed to receive the head of the patient and the second and third measuring rings being positionable to a position corresponding to a portion of the receiving area designed to receive the bust of the patient,
wherein the first measuring ring is a scintillation type and having an internal diameter less than an internal diameter of the second measuring ring and less than an internal diameter of the third measuring ring,
wherein the second measuring ring is designed to perform only a PET type investigation and comprises an annular outer case and a succession of scintillation elements located within the annular outer case,
wherein the third measuring ring is designed to perform only a SPECT type investigation, and
wherein said second and third measuring rings are configured to be selectively activated or deactivated depending upon a specific detection to be carried out on the patient, with the activated ring being moved into position for the specific detection while the deactivated ring does not move and remains above the head level of the patient.

18. The device according to claim 17, wherein the measuring rings are slidably mounted on the support structure to individually and independently slide along the support structure in such a way as to selectively move one of the rings while the other rings are not moved.

19. The device according to claim 17, wherein,
the second measuring ring is designed to perform the PET type investigation and comprises the annular outer case and the succession of scintillation elements located within the annular outer case, the succession of scintillation elements being movable laterally by rotating around the receiving area in such a way as to acquire at least two images rotated between each other by a predetermined angle, and
the third measuring ring is designed to perform a SPECT type investigation and comprises another annular outer case and another succession of scintillation elements associated with a collimator and included inside the another annular outer case, the another succession of scintillation elements being movable laterally by rotating around the receiving area in such a way as to acquire at least two further images rotated between each other by a predetermined angle.

20. The device according to claim 17, wherein, each of the measuring rings is axisymmetric in shape about a common axis that coincides with a direction of extension of the receiving area, such that the each of the measuring rings extend on a circular line, adopting a toroidal shape, wherein the support structure supports the first measuring ring (5) above the second and third measuring rings, the measuring rings being independently movable along a common axis, and the second measuring ring is structured to performs the PET type investigation for dedicated organs while the third measuring ring performs only one morphological investigation other than the PET type investigation.

* * * * *